US008642099B2

(12) United States Patent
Erdelmeier et al.

(10) Patent No.: US 8,642,099 B2
(45) Date of Patent: Feb. 4, 2014

(54) METHOD FOR PREPARING GINKGO EXTRACTS HAVING A LOW CONTENT OF 4'-O-METHYL PYRIDOXINE AND/OR BIFLAVONES

(75) Inventors: Clemens Erdelmeier, Karlsruhe (DE); Hermann Hauer, Karlsruhe (DE); Egon Koch, Karlsruhe (DE); Friedrich Lang, Hagenbach (DE)

(73) Assignee: Dr. Willmar Schwabe GmbH & Co. KG, Karlsruhe (DE)

( * ) Notice: Subject to any disclaimer, the term of this patent is extended or adjusted under 35 U.S.C. 154(b) by 740 days.

(21) Appl. No.: 12/217,803

(22) Filed: Jul. 9, 2008

(65) Prior Publication Data
US 2008/0286391 A1 Nov. 20, 2008

Related U.S. Application Data

(62) Division of application No. 11/416,924, filed on May 2, 2006, now abandoned.

(30) Foreign Application Priority Data

May 3, 2005 (DE) .......................... 10 2005 020 685
Dec. 23, 2005 (DE) .......................... 10 2005 061 948

(51) Int. Cl.
*A61K 35/16* (2006.01)

(52) U.S. Cl.
USPC ....................................................... 424/752

(58) Field of Classification Search
None
See application file for complete search history.

(56) References Cited

U.S. PATENT DOCUMENTS

| 4,981,688 | A | 1/1991 | Ayroles et al. | |
| 5,399,348 | A | 3/1995 | Schwabe | |
| 6,328,999 | B1 * | 12/2001 | Schwabe | 424/752 |
| 2004/0076691 | A1 * | 4/2004 | Haines et al. | 424/729 |

FOREIGN PATENT DOCUMENTS

| DE | 39 40 091 C2 | 6/1991 |
| EP | 0 360 556 A1 | 3/1990 |
| EP | 1 037 646 B1 | 9/2000 |
| JP | A-1258626 | 10/1989 |
| JP | A 7-138171 | 5/1995 |

OTHER PUBLICATIONS

Food Chemicals Index. Institute of Medicine (U.S.) Committee on Food Chemicals. National Academic Press. 2003. p. 835.*
Xu et al. Synthesis of the Adsorbent Based on Macroporous Copolymer MA-DVD Beads and Its Application in Purification for the Extracts of Ginkso Biloba Leaves. Reactive & Functional Polymers 43 (2000) 297-304.*
Harris. Quantitative Chemical Analysis. Macmillan 2003. p. 598.*
T. van Beek, "Chemical analysis of Ginkgo biloba leaves and extracts", Journal of Chromatography A, 967:21-55 (2002).
A. Arenz et al., "Occurrence of Neurotoxic 4'-O-Methylpyridoxine in Ginkgo biloba Leaves, Ginkgo Medications and Japanese Ginkgo Food", Planta Med., vol. 62, No. 6, pp. 548-551 (1996).
S. Kressman et al., "Pharmaceutical Quality of Different Ginkgo biloba Brands", Journ. of Pharm. and Pharm., vol. 54, No. 5, pp. 661-669 (2002).
T.A. van Beek et al., "Ginkgo biloba L", Fitoterapia, IDB Holding, Milan, Italy, vol. LXIX, No. 3, pp. 195-244 (1998).
Z. Zhang, "Powder injection of ginko and dipyridamole and its preparing method", English abstract of CN 1 557 455, XP-002398187 (2004).

* cited by examiner

*Primary Examiner* — Chris R Tate
*Assistant Examiner* — Russell Fiebig
(74) *Attorney, Agent, or Firm* — Edwards Wildman Palmer LLP; Peter F. Corless; Christine C. O'Day

(57) ABSTRACT

The present invention relates to an improved multi-step method for preparing an extract from ginkgo biloba having a reduced content of 4'-O-methyl pyridoxine and/or biflavones, wherein the depletion is carried out by filtration over an adsorber resin and/or an ion exchanger and the substances to be removed are retained on the resin. The invention further relates to an extract from ginkgo biloba having a reduced content of 4'-O-methyl pyridoxine and/or biflavones, which is obtainable by the method according to the present invention, as well as to its use.

8 Claims, No Drawings

METHOD FOR PREPARING GINKGO EXTRACTS HAVING A LOW CONTENT OF 4'-O-METHYL PYRIDOXINE AND/OR BIFLAVONES

The present invention relates to an improved multi-step method for preparing an extract from ginkgo biloba having a reduced content of 4'-O-methyl pyridoxine and/or biflavones, wherein the depletion is effected by filtration over an adsorber resin and/or an ion exchanger and the substances to be removed are retained on the resin. The invention further relates to an extract from ginkgo biloba having a reduced content of 4'-O-methyl pyridoxine and/or biflavones which is obtainable by the method according to the present invention, as well as to its use.

Since decades, extracts from the leaves of ginkgo biloba are used as a medicament. They are currently used for the treatment of different kinds of dementia and symptoms thereof as well as cerebral and peripheral blood circulation disorders. Ingredients, the efficacy is associated with, are terpene lactones (ginkgolides A, B, C and bilobalide) as well as glycosides of flavones (quercetin, kaempferol and isorhamnetin). The leaves of ginkgo biloba also contain components which do not contribute to the desired efficacy, but which may be responsible for risks and side effects. In addition to unpolar plant ingredients such as ginkgolic acids, those components are 4'-O-methyl pyridoxine and biflavones. In a ginkgo extract, which is efficacious and at the same time as safe as possible and as low in side effects as possible, these compounds should thus not be present to the largest possible extent.

4'-O-methyl pyridoxine may cause symptoms of poisoning such as convulsive seizures and unconsciousness. Thus, this compound is also referred to as ginkgotoxin. The biflavones contained in ginkgo exhibit an immunotoxic potential and may elicit contact allergies. These biflavones contained in ginkgo are predominantly the compounds amentoflavone, bilobetin, ginkgetin, isoginkgetin and sciadopitysin.

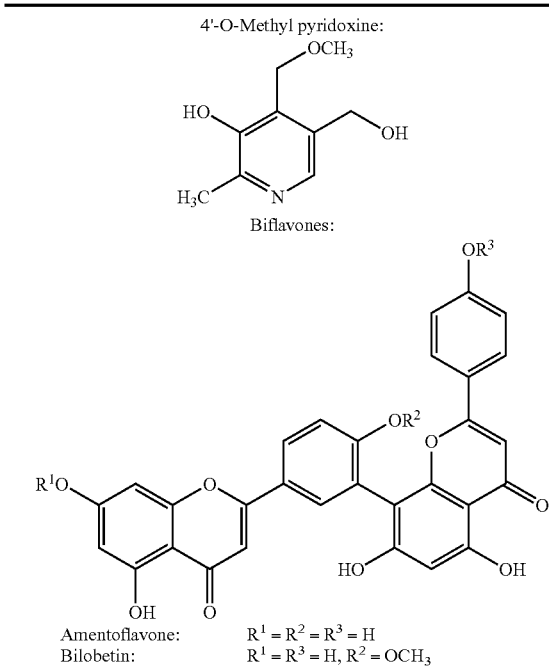

Amentoflavone: $R^1 = R^2 = R^3 = H$
Bilobetin: $R^1 = R^3 = H, R^2 = OCH_3$
Ginkgetin: $R^3 = H, R^1 = R^2 = OCH_3$
Isoginkgetin: $R^1 = H, R^2 = R^3 = OCH_3$
Sciadopitysin: $R^1 = R^2 = R^3 = OCH_3$ Methods for depleting 4'-O-methyl pyridoxine and simultaneously biflavones as well as the extracts obtained are already described in EP 1 037 646 B1. Therein, 4'-O-methyl pyridoxine is retained using an acidic cation exchanger and the biflavones are adsorbed on activated carbon. Preferably these depletion steps are carried out after step f) of the method according to EP 1 037 646 B1 (page 3), i.e., after "treating the solution with a lead compound or an insoluble polyamide". The method of EP 1 037 646 B1 is based on the method originally described in DE 39 40 091 C2.

In EP 1 037 646 B1 the depletion of the biflavones and 4'-O-methyl pyridoxine is carried out at a stage of the method (step f)), wherein relatively high contents of lead salts and ammonium salts are present such that an increased amount of ion exchanger has to be employed.

Furthermore, the depletions of biflavones and 4'-O-methyl pyridoxine are described and claimed in combination only. However, depending on the limits to be possibly established in the future and in view of the requirement of as low a modification of the extract composition as possible, it may be desirable to remove the biflavones or 4'-O-methyl pyridoxine only.

Furthermore, the contents of less than 50 ppm of 4'-O-methyl pyridoxine and less than 100 ppm of biflavones which are aspired in EP 1 037 646 B1, are still comparatively high. Since EP 1 037 646 B1 does not describe a comparative example, also the actual degree of depletion achieved in Examples 2 and 3 cannot be seen from this reference.

Thus, it is the object underlying the present invention to provide a method for preparing ginkgo extracts having a low content of 4'-O-methyl pyridoxine and/or a low content of bioflavones which does not have the disadvantages indicated above and, in particular, wherein well recyclable and/or very inexpensive adsorbents are employed, which leads to contents of 4'-O-methyl pyridoxine of less than 20 ppm, preferably less than 10 ppm and particularly preferred less than 2 ppm and/or contents of biflavones of less than 20 ppm, preferably less than 10 ppm and particularly preferred less than 5 ppm and which leads to extracts having preferred contents of flavonoides of 20 to 30% by weight (particularly preferred 22.0 to 27.0%), of terpene lactones of 4.5 to 8.5% by weight (particularly preferred 5.0 to 7.0%, preferably 2.8 to 3.4% ginkgolides A, B and C and 2.6 to 3.2% bilobalid) and of ginkgolic acids (5 ppm at the most), wherein said contents of flavonoids of 22.0 to 27.0%, of terpene lactones of 5.0 to 7.0% (2.8 to 3.4% thereof ginkgolides A, B and C and 2.6 to 3.2% thereof bilobalid) and of ginkgolic acids (5 ppm at the most) fulfil the requirements of the German Pharmacopoeia 2003 ("Deutsches Arzneibuch"; DAB).

According to the DAB the flavonoids are determined in the form of quercetin, kaempferol and isorhamnetin after acidic hydrolysis and calculated as flavonoid glycosides.

This object could be solved by separating the biflavones using adsorber resins and/or separating 4'-O-methyl pyridoxine via acidic ion exchangers.

In order to produce the extracts according to the present invention, preferably the following method is carried out, wherein steps a) to i) as well as m) are essentially described already in DE 39 40 091 C2, the total disclosure content of which, in particular with respect to the details of the method, shall be incorporated into the present application by reference:

a) extracting the leaves of ginkgo biloba (drug) at a temperature of 20-100° C., preferably 40-60° C., using water-containing acetone having a content of 20-90% by weight, a water-containing alkanol having 1 to 3 carbon atoms (methanol, ethanol, n-propanol and isopropanol) and a content of 20-90% by weight or anhydrous methanol, wherein the ratio drug: solvent amounts to 1:4 to 1:20, preferably 1:5 to 1:10, b) separating the organic solvent by evaporating the solvent to a content of 10% by weight at the most (preferably 5% by weight at the most), wherein water may be added during the final distillation steps, c) diluting the remaining aqueous solution with water to a solids content of 5 to 25% by weight (preferably 15 to 20% by weight), cooling the solution to a temperature below 25° C. (preferably about 10 to 12° C.) and allowing the remaining aqueous solution to stand until a precipitation is formed, d) treating the remaining aqueous solution with ammonium sulfate (preferably to a content of up to 40% by weight, particularly preferred 25 to 35% by weight) and subsequently extracting the solution at least once using methyl ethyl ketone or a mixture of methyl ethyl ketone and acetone (preferably in a ratio of 9:1 to 4:6, in particular 6:4), e) concentrating the extract obtained (preferably to a solids content of 50 to 70% by weight) and diluting the extract with a mixture of ethanol and water to obtain a solution containing 50% by weight water and 50% by weight ethanol and having a solids content of 10% by weight, f) treating the solution with a lead compound (preferably with lead acetate, lead hydroxide acetate, lead nitrate or an aqueous suspension of lead hydroxide) until a change in colour from brown to umber occurs, or an insoluble polyamide (preferably polyamide 6, polyamide 6,6 or crosslinked polyvinylpyrrolidone (polyvidone)), g) extracting the filtered solution using an aliphatic or cycloaliphatic solvent having a boiling point of 60 to 100° C., h) concentrating the remaining aqueous-alcoholic solution, subsequently treating is the solution with ammonium sulfate and extracting the solution with methyl ethyl ketone and ethanol, (the solution is preferably concentrated under reduced pressure to an ethanol content of about 5% at the most, added with ammonium sulfate to a content of 20% by weight and extracted with the solvent in a ratio of 8:2 to 5:5, preferably 6:4), i) concentrating the organic phase obtained to a solids content of 50 to 70% by weight, k) dissolving the concentrate in an aqueous alkanol having 1 to 3 carbon atoms and optionally filtering the product, l) filtration over an adsorber resin and/or an ion exchanger, wherein the substances to be removed are retained on the resin and m) drying the concentrate (preferably at a maximum temperature of 60 to 80° C.) under reduced pressure to obtain a dry extract having a water content of less than 5%.

It is the advantage of the method according to the present invention that the depletion step is carried out at the end of the method. Thus, a smaller amount of the ion exchanger has to be employed and particularly low contents of 4'-O-methyl pyridoxine and/or biflavones are obtained.

Preferred adsorber resins in step l) are resins based on optionally substituted styrenes/divinylbenzenes such as Diaion HP-20, HP-21 or Sepabeads SP-207 and SP-850. Preferred ion exchangers are strongly acidic ion exchangers such as Merck I or Amberlite IR-120. The filtration optionally includes the usual rinsing using further solvent. The aqueous alkanol in step k) is aqueous methanol, ethanol, n-propanol or isopropanol having a content of 20-90% by weight, respectively, preferably aqueous ethanol, a concentration of 40 to 60% by weight being particularly preferred.

A subject of the present invention are extracts, in particular dry extracts, which are obtainable by the method according to the present invention and which exhibit the following contents:

less than 20 ppm, preferably less than 10 ppm and in particular less than 2 ppm 4'-O-methyl pyridoxine and/or less than 20 ppm, preferably less than 10 ppm and in particular less than 5 ppm biflavones.

Furthermore, subject of the present invention are extracts, in particular dry extracts, which are obtainable by the method according to the present invention and which exhibit the following further contents:

20 to 30% by weight, preferably 22.0 to 27.0% by weight flavonoids, 4.5 to 8.5% by weight, preferably 5.0 to 7.0% by weight terpene lactones and less than 10 ppm, preferably not more than 5 ppm ginkgolic acids.

A further subject of the present invention are extracts, in particular dry extracts, which are obtainable by the method according to the present invention and which exhibit the following contents:

20 to 30% by weight, preferably 22.0 to 27.0% by weight flavonoids, 2.5 to 4.5% by weight ginkgolides A, B and C in total, preferably 2.8 to 3.4% by weight ginkgolides A, B and C in total, 2.0 to 4.0% by weight, preferably 2.6 to 3.2% by weight bilobalide, less than 10 ppm, preferably not more than 5 ppm ginkgolic acids and less than 20 ppm, preferably less than 10 ppm, particularly preferred less than 2 ppm of 4'-O-methyl pyridoxine and/or less than 20 ppm, preferably less than 10 ppm and particularly preferred less than 5 ppm of biflavones.

According to the European Pharmacopoeia, dry extracts generally have a dry residue of at least 95% by weight.

The extracts according to the present invention can be administered in the form of powders, granules, tablets, dragées (coated tablets) or capsules, preferably orally. In order to prepare tablets, the extract is mixed with suitable pharmaceutically acceptable adjuvants such as lactose, cellulose, silicon dioxide, croscarmellose and magnesium stearate, and pressed into tablets which are optionally provided with a suitable coating, for example made of hydroxymethylcellulose, polyethyleneglycol, pigments (such as titanium dioxide, iron oxide) and talcum. The extract according to the present invention can also be filled into capsules, optionally under the addition of adjuvants such as stabilizers, fillers and the like. The dosage is such that 10 to 2000 mg, preferably 50 to 1000 mg and particularly preferred 100 to 500 mg extract are administered per day.

A further subject of the present invention are medicaments, food products and other preparations containing these extracts, optionally in combination with other substances such as active ingredients and/or pharmaceutically acceptable adjuvants. The term "food product" as used herein particularly refers to dietetic food products, dietary supplement products as well as medical food and dietary supplements.

EXAMPLES

Preparation of the Extract Solution Used in Examples 1 and 2 as Well as in Comparative Examples 1 and 2

Dried leaves of ginkgo biloba (drug) were extracted at a temperature of about 50° C. using seven times their weight (w/w) (i.e. drug-solvent ratio is 1:7) made up of acetone/water 60/40 (w/w) (step a)).

The organic solvent was largely separated from the extract (step b)) and the remaining concentrated aqueous solution was diluted with water to a solids content of about 10% by weight. The solution was cooled to a temperature of about 12° C. under agitation and the resulting precipitate was removed (step c)).

About 30% by weight ammonium sulfate was added to the remaining aqueous solution and the solution formed was extracted using a mixture of methyl ethyl ketone and acetone in a ratio of 6:4 (step d)).

The extract obtained was largely concentrated and the concentrate thus obtained was diluted with water and ethanol such that a solution containing 50% by weight water and 50% by weight ethanol at a solids content of about 10% by weight was obtained (step e)). The solution was filtered and the filtrate was added with an aqueous solution of lead hydroxide acetate (step f)).

After a further filtration, the remaining aqueous alcoholic solution was extracted with heptane (step g)).

Subsequently, the remaining aqueous alcoholic solution was concentrated under reduced pressure to an ethanol content of about 5% and ammonium sulfate was added such that a content of about 20% by weight based on the water content was achieved.

The solution obtained was extracted using a mixture of methyl ethyl ketone and ethanol in a ratio of 6:4 (step h)).

The resulting organic phase was largely concentrated (solids content of about 55% by weight) (step i)). Then the product was diluted with ethanol and water such that a solution having an ethanol content of about 75% and a solids content of about 15% was obtained (step k)).

Example 1

Ginkgo Extract Having a Reduced Content of 4'-O-methyl Pyridoxine 1249 g of the extract solution obtained according to the preparation method described above was adjusted with water to an ethanol content of about 40% (w/w) and applied to 50 ml (corresponding to 0.28 ml/g of the dry extract) Amberlite IR-120 (strongly acidic ion exchanger) (column: about 2×16.5 cm; flow: about 8 ml/min) (step 1)), followed by rinsing with 200 ml of 50% ethanol (w/w). The resulting solution was concentrated on a rotary evaporator and dried in vacuum at 50° C. (step m)): 179.4 g.

As can be seen from the following table, a content of 4'-O-methyl pyridoxine of 0.4 ppm was achieved without essentially modifying the contents of ingredients which are relevant with respect to the efficacy.

Comparative Example 1

Ginkgo Extract without Depletion According to Step 1) of the Present Invention 98.4 g of the extract solution employed in Example 1 were concentrated by evaporation and dried in vacuum at 50° C.: 14.7 g.

Example 2a)

Ginkgo Extract Having a Reduced Content of Biflavones 500 g of the extract solution obtained according to the preparation method described above were adjusted with water to an ethanol content of about 40% (w/w) and applied to 400 ml (corresponding to 5.7 ml/g of the dry extract) Sepabeads SP-850 (adsorber resin) (column: about 4×32 cm; flow: about 8 ml/min) (step 1)), followed by rinsing with about 2 l of 40% ethanol (w/w) in total. 10% of the resulting solution (259.3 g) were concentrated on a rotary evaporator and freeze-dried (step m)): 6.92 g. The remaining 90% of the solution were employed in Example 2b).

As can be seen from the following table, biflavone contents of less than 1 ppm were achieved, respectively, without essentially modifying the contents of ingredients which are relevant with respect to the efficacy.

Example 2b)

Ginkgo Extract Having a Reduced Content of 4'-O-methyl Pyridoxine and Biflavones 90% of the solution obtained in Example 2a) (2334.1 g) were applied to 25 ml (corresponding to 0.40 ml/g of the dry extract) Amberlite IR-120 (strongly acidic ion exchanger) (column: about 1.5×11 cm; flow: about 10 ml/min) (step 1)), followed by rinsing with 100 ml of 40% ethanol (w/w). The resulting solution was concentrated on a rotary evaporator and freeze-dried (step m)): 61.67 g.

As can be seen from the following table, a content of 4'-O-methyl pyridoxine of 0.4 ppm and contents of biflavones of less than 1 ppm were achieved, respectively, without essentially modifying the contents of ingredients that are relevant with respect to the efficacy.

Comparative Example 2

Ginkgo Extract without Depletion According to Step 1) of the Present Invention 50 g of the extract solution employed in Example 2a) were concentrated by evaporation and freeze-dried: 7.05 g.

Comparative Example 3

Ginkgo Extract with Biflavone Depletion and 4'-O-methyl Pyridoxine Depletion after Treatment with a Lead Compound (step f)) According to EP 1 037 646 B1

Dried leaves of ginkgo biloba (drug) were extracted at a temperature of about 50° C. using seven times their weight (w/w) (i.e. drug-solvent ratio is 1:7) made up of acetone/water 60/40 (w/w).

The organic solvent was largely separated from the extract and the remaining concentrated aqueous solution was diluted with water to a solids content of about 10% by weight, cooled to a temperature of about 12° C. under agitation and the resulting precipitate was removed.

About 30% by weight ammonium sulfate was added to the remaining aqueous solution and the solution formed was extracted using a mixture of methyl ethyl ketone and acetone in a ratio of 6:4.

The extract obtained was largely concentrated and the concentrate thus obtained was diluted with water and ethanol such that a solution containing 50% by weight water and 50% by weight ethanol at a solids content of about 10% by weight was obtained. The solution was filtered, the filtrate was added with an aqueous solution of lead hydroxide acetate and filtered again (step f)).

150 ml of the solution thus obtained (portion of dry extract: 7.1%; ethanol content: about 50%) were stirred with 2.5 g (corresponding to 0.17 g/g of the final product) active carbon for 30 minutes at room temperature. The filtrate was applied to a column with 4.2 ml (corresponding to 0.28 ml/g of the final product) strongly acidic cation exchanger (Merck I). The ion exchanger column was washed with 4×5 ml EtOH (50%).

The combined eluates were extracted by shaking using 3×70 ml n-hexane. The ethanol/water phase was concentrated on a rotary evaporator and diluted with water to 100 g. The extract solution thus obtained was extracted with 1×40 ml, 2×30 ml and 1×20 ml of a mixture of methyl ethyl ketone: ethanol in a ratio of 3:2, wherein 15 g ammonium sulfate was added to achieve phase separation.

The organic phase was stirred for 1 h at room temperature after adding 25 g ammonium sulfate. The undissolved ammonium sulfate as well as the aqueous phase formed were separated. The extract solution was concentrated on a rotary evaporator at 50° C. and dried in vacuum at 60° C.: 14.8 g.

As can be seen from the following table, a 4'-O-methyl pyridoxine content of 52 ppm and a biflavone content of 31.3 ppm and, thus, significantly higher contents and inferior depletion results are achieved compared to Example 2b) according to the present invention.

The determination of the contents of flavonoids, terpene lactones and ginkgolic acids listed in Table 1 was carried in accordance with the DAB.

The quantitative determination of 4'-O-methyl pyridoxine was performed by means of HPLC and fluorescence detection after enrichment via Sep Pak Plus C18 cartridges, followed by enrichment via Bond Elut LRC-SCX cartridges, wherein a Phenomenex Prodigy 5μ ODS-3 HPLC column and a gradient of trifluoroacetic acid (pH 2): methanol=9:1 (v/v) →methanol, were employed.

The determination of the contents of the biflavones listed in Table 1 was performed by means of HPLC and UV detection at 340 nm via a Waters Nova Pak C18 column using a gradient of water: acetonitrile of 9:1 (v/v)+0.3% by volume phosphoric acid (85%)→acetonitrile+0.3% by volume phosphoric acid.

In each case, calibration was performed using reference substances having a high, defined purity grade.

TABLE 1

Composition of the extracts according to examples given above

| Extract according to | Example 1 | Comparative Example 1 | Example 2a) | Example 2b) | Comparative Example 2 | Comparative Example 3 |
|---|---|---|---|---|---|---|
| Flavonoids [%] | 24.86 | 24.51 | 27.17 | 25.32 | 25.89 | 22.78 |
| Ginkgolides A, B, C [%] | 3.28 | 2.94 | 2.97 | 3.04 | 2.97 | 3.40 |
| Bilobalide [%] | 3.17 | 3.03 | 3.18 | 3.14 | 3.07 | 3.07 |
| Terpene lactones [%] | 6.45 | 5.97 | 6.15 | 6.18 | 6.04 | 6.47 |
| Ginkgolic acids [ppm] | <5 | <5 | <5 | <5 | <5 | <5 |
| 4'-O-Methyl pyridoxine [ppm] | 0.4 | 104.5 | 164 | 0.8 | 89 | 52 |
| Amentoflavone [ppm] | 68.5 | 78.7 | n.d. (<1) | n.d. (<1) | 81.6 | 12.6 |
| Bilobetin [ppm] | 123.3 | 120.4 | n.d. (<1) | n.d. (<1) | 136.4 | 10.4 |
| Ginkgetin [ppm] | 86.3 | 82.1 | n.d. (<1) | n.d. (<1) | 86.1 | 2.7 |
| Isoginkgetin [ppm] | 103.3 | 104.4 | n.d. (<1) | n.d. (<1) | 111.5 | 4.8 |
| Sciadopitysin [ppm] | 44.0 | 43.0 | n.d. (<1) | n.d. (<1) | 44.0 | 0.8 |
| Total amount of biflavones [ppm] | 425.4 | 428.6 | n.d. (<5) | n.d. (<5) | 459.6 | 31.3 | n.d. = not detectable

The invention claimed is:

1. A method for producing an extract of ginkgo biloba having a reduced content of 4'-O-methyl pyridoxine and biflavones, comprising the steps of:
   a) extracting leaves of ginkgo biloba with an organic solvent, wherein said organic solvent is selected from aqueous acetone, aqueous alcohol having 1 to 3 carbon atoms and anhydrous methanol, to obtain an extract mixture,
   b) separating the organic solvent from the extract mixture to produce a crude extract,
   c) diluting the crude extract with water to produce an aqueous solution with a solids content of 5 to 25% by weight, cooling to a temperature below 25° C. and allowing to stand until a precipitate is formed and removing the precipitate from the aqueous solution,
   d) adding about 30% by weight ammonium sulfate to the aqueous solution and extracting with a mixture of methyl ethyl ketone and acetone to produce an extract solution,
   e) concentrating the extract solution and diluting with an ethanol-water mixture to obtain a solution containing 50% by weight water and 50% by weight ethanol at a solids content of 10% by weight to produce a reaction mixture,
   f) adding an aqueous solution of lead hydroxide acetate and filtering the reaction mixture to obtain a filtered solution,
   g) extracting the filtered solution with an aliphatic or cycloaliphatic solvent having a boiling point of 60 to 100° C. to obtain an aqueous-alcoholic solution,
   h) concentrating the aqueous-alcoholic solution under reduced pressure to an alcohol content of about 5% and adding about 30% by weight ammonium sulfate to the aqueous solution and extracting with a mixture of methyl ethyl ketone and ethanol to obtain an organic phase, i) concentrating the organic phase to a solids content of 50 to 70% by weight to obtain a concentrate, j) diluting the concentrate obtained in step i) with aqueous alcohol having 1 to 3 carbon atoms to obtain an aqueous alcohol mixture with a solids content of about 15% and optionally filtering the aqueous alcohol mixture to remove undissolved substances, k) filtering the aqueous alcohol mixture obtained in step j) over an adsorber resin and a strongly acidic ion exchanger, wherein said adsorber resin is based on one or more optionally substituted styrene and/or divinylbenzene and wherein the substances to be removed are retained on the resin to obtain a purified solution, and l) drying the purified solution at reduced pressure to obtain a dry ginkgo biloba extract with a water content less than 5%, wherein the extract contains less than 20 ppm 4'-O-methyl pyridoxine and/or less than 20 ppm biflavones.

2. The method of claim 1 wherein the aqueous alcohol in step j) is aqueous ethanol.

3. The method of claim 2 wherein the aqueous ethanol is ethanol having a content of 40 to 60% by weight.

4. A method for producing an extract of ginkgo biloba having a reduced content of 4'-O-methyl pyridoxine and biflavones, comprising the steps of:

a) extracting leaves of ginkgo biloba with an organic solvent, wherein said organic solvent is selected from aqueous acetone, aqueous alcohol having 1 to 3 carbon atoms and anhydrous methanol, to obtain an extract mixture, b) separating the organic solvent from the extract mixture to produce a crude extract, c) diluting the crude extract with water to produce an aqueous solution with a solids content of 5 to 25% by weight, allowing to stand until a precipitate is formed and removing the precipitate from the aqueous solution, d) adding about 30% by weight ammonium sulfate to the aqueous solution and extracting with a mixture of methyl ethyl ketone and acetone to produce an extract solution, e) concentrating the extract solution and diluting with an ethanol-water mixture to obtain a solution having a solids content of 10% by weight to produce a reaction mixture, f) adding an aqueous solution of lead hydroxide acetate to obtain a solution, g) extracting the solution obtained in step f) with an aliphatic or cycloaliphatic solvent to obtain an aqueous-alcoholic solution, h) concentrating the aqueous-alcoholic solution under reduced pressure to an alcohol content of about 5% and adding about 30% by weight ammonium sulfate to the aqueous solution and extracting with a mixture of methyl ethyl ketone and ethanol to obtain an organic phase, i) concentrating the organic phase to a solids content of 50 to 70% by weight to obtain a concentrate, j) diluting the concentrate obtained in step i) with aqueous alcohol having 1 to 3 carbon atoms to obtain an aqueous alcohol mixture with a solids content of about 15% and optionally filtering the aqueous alcohol mixture to remove undissolved substances, k) filtering the aqueous alcohol mixture obtained in step j) over an adsorber resin and a strongly acidic ion exchanger, wherein said adsorber resin is based on one or more optionally substituted styrene and/or divinylbenzene to obtain a purified solution, and l) drying the purified solution at reduced pressure to obtain a dry ginkgo biloba extract with a water content less than 5%, wherein the extract contains less than 20 ppm 4'-O-methyl pyridoxine and/or less than 20 ppm biflavones.

5. The method of claim 1 wherein the extract comprises less than 10 ppm 4'-O-methyl pyridoxine.

6. A method for producing an extract of ginkgo biloba having a reduced content of biflavones, comprising the steps of:

a) extracting leaves of ginkgo biloba with an organic solvent, wherein said organic solvent is selected from aqueous acetone, aqueous alcohol and anhydrous methanol, to obtain an extract mixture, b) separating the organic solvent from the extract mixture to produce a crude extract, c) diluting the crude extract with water to produce an aqueous solution with a solids content of 5 to 25% by weight, cooling to a temperature below 25° C. and allowing to stand until a precipitate is formed and removing the precipitate from the aqueous solution, d) adding about 30% by weight ammonium sulfate to the aqueous solution and extracting with a mixture of methyl ethyl ketone and acetone to produce an extract solution, e) concentrating the extract solution and diluting with an ethanol-water mixture to obtain a solution with a solids content of 10% by weight to produce a reaction mixture, f) adding an aqueous solution of lead hydroxide acetate and filtering the reaction mixture to obtain a filtered solution, g) extracting the filtered solution with an aliphatic or cycloaliphatic solvent having a boiling point of 60 to 100° C. to obtain an aqueous-alcoholic solution, h) concentrating the aqueous-alcoholic solution under reduced pressure to an alcohol content of about 5% and adding about 30% by weight ammonium sulfate to the aqueous solution and extracting with a mixture of methyl ethyl ketone and ethanol to obtain an organic phase, i) concentrating the organic phase to a solids content of 50 to 70% by weight to obtain a concentrate, j) diluting the concentrate obtained in step i) with aqueous alcohol having 1 to 3 carbon atoms to obtain an aqueous alcohol mixture with a solids content of about 15% and optionally filtering the aqueous alcohol mixture, k) filtering the aqueous alcohol mixture obtained in step j) over an adsorber resin, wherein said adsorber resin is based on one or more optionally substituted styrene and/or divinylbenzene and wherein the substances to be removed are retained on the resin to obtain a purified solution, and l) drying the purified solution at reduced pressure to obtain a dry ginkgo biloba extract with a water content less than 5%, wherein the extract contains less than 20 ppm 4'-O-methyl pyridoxine and/or less than 20 ppm biflavones.

7. The method of claim 6, wherein the adsorber resin in step k) is a copolymer of styrene and divinylbenzene.

8. A method for producing an extract from ginkgo biloba having a reduced content of 4'-O-methyl pyridoxine, comprising the steps of:

a) extracting leaves of ginkgo biloba with an organic solvent, wherein said organic solvent is selected from aqueous acetone, aqueous alcohol and anhydrous methanol, to obtain an extract mixture, b) separating the organic solvent from the extract mixture to produce a crude extract, c) diluting the crude extract with water to produce an aqueous solution with a solids content of 5 to 25% by weight, cooling to a temperature below 25° C. and allowing to stand until a precipitate is formed and removing the precipitate from the aqueous solution, d) adding about 30% by weight ammonium sulfate to the aqueous solution and extracting with a mixture of methyl ethyl ketone and acetone to produce an extract solution, e) concentrating the extract solution and diluting with an ethanol-water mixture to obtain a solution with a solids content of 10% by weight to produce a reaction mixture, f) adding an aqueous solution of lead hydroxide acetate and filtering the reaction mixture to obtain a filtered solution, g) extracting the filtered solution with an aliphatic or cycloaliphatic solvent having a boiling point of 60 to 100° C. to obtain an aqueous-alcoholic solution, h) concentrating the aqueous-alcoholic solution under reduced pressure to an alcohol content of about 5% and adding about 30% by weight ammonium sulfate to the aqueous solution and extracting with a mixture of methyl ethyl ketone and ethanol to obtain an organic phase, i) concentrating the organic phase to a solids content of 50 to 70% by weight to obtain a concentrate, j) diluting the concentrate obtained in step i) with aqueous alcohol having 1 to 3 carbon atoms to obtain an aqueous alcohol mixture with a solids content of about 15% and optionally filtering the aqueous alcohol mixture, k) filtering the aqueous alcohol mixture obtained in step j) over an adsorber resin, wherein said adsorber resin is based on one or more optionally substituted styrene and/or divinylbenzene and wherein the substances to be removed are retained on the resin to obtain a first purified solution, l) filtering the first purified solution over a strongly acidic ion exchanger, wherein the substances to be removed are retained on the ion exchanger to obtain a second purified solution, and m) drying the second purified solution at reduced pressure to obtain a dry extract having a water content of less than 5%, wherein the extract contains less than 20 ppm 4'-O-methyl pyridoxine and/or less than 20 ppm biflavones.

* * * * *